US012653411B2

(12) United States Patent
Sung et al.

(10) Patent No.: US 12,653,411 B2
(45) Date of Patent: Jun. 16, 2026

(54) HEART RATE DETECTION DEVICE AND METHOD

(71) Applicant: Quanta Computer Inc., Taoyuan City (TW)

(72) Inventors: Jia-Li Sung, Taoyuan City (TW); Peng-Zhe Tsai, Taoyuan City (TW); Yung-Ming Chung, Taoyuan City (TW)

(73) Assignee: QUANTA COMPUTER INC., Taoyuan City (TW)

( * ) Notice: Subject to any disclaimer, the term of this patent is extended or adjusted under 35 U.S.C. 154(b) by 473 days.

(21) Appl. No.: 18/321,883

(22) Filed: May 23, 2023

(65) Prior Publication Data

US 2024/0237908 A1      Jul. 18, 2024

(30) Foreign Application Priority Data

Jan. 17, 2023      (TW) .................................. 112101958

(51) Int. Cl.
*A61B 5/0245*          (2006.01)
*A61B 5/308*          (2021.01)
*A61B 5/352*          (2021.01)

(52) U.S. Cl.
CPC ............ *A61B 5/0245* (2013.01); *A61B 5/308* (2021.01); *A61B 5/352* (2021.01)

(58) Field of Classification Search
CPC ........ A61B 5/0245; A61B 5/352; A61B 5/308
See application file for complete search history.

(56) References Cited

U.S. PATENT DOCUMENTS

2011/0184296 A1* 7/2011 Vajdic .................. A61B 5/7221
600/509

* cited by examiner

*Primary Examiner* — Lindsey G Wehrheim
(74) *Attorney, Agent, or Firm* — McClure, Qualey & Rodack, LLP

(57) ABSTRACT

An embodiment of the invention provides a heart rate detection device. The heart rate detection device may include an electrocardiography (ECG) signal extraction circuit, a detection circuit, a calculation circuit and a filter. The ECG signal extraction circuit obtains an ECG signal. The detection circuit detects a plurality of R-waves in the ECG signal. The calculation circuit uses the first of the R-waves as the initial point from which to calculate the standard deviation of the R-waves in each moving window. The calculation circuit determines whether the standard deviation corresponding to each moving window is larger than the first threshold. The calculation circuit determines whether the number of moving windows whose corresponding standard deviation exceeds the first threshold is larger than a second threshold to generate a determination result. Furthermore, the calculation circuit determines whether to use the filter to filter the ECG signal based on the determination result.

8 Claims, 4 Drawing Sheets

A initial point initial point

HEART RATE DETECTION DEVICE AND METHOD

CROSS REFERENCE TO RELATED APPLICATIONS

This Application claims priority of TW Patent Application No. 112101958 filed on Jan. 17, 2023, the entirety of which is incorporated by reference herein.

BACKGROUND OF THE INVENTION

Field of the Invention

The invention generally relates to heart rate detection technology, and more particularly, to a heart rate detection technology for determining whether to use a filter to filter the T-waves in an Electrocardiography (ECG) signal.

Description of the Related Art

As science and medical technology continue to progress, the requirements on measuring and analyzing physiological signals are becoming more stringent. An ECG is a diagnostic and treatment technology in which the electrophysiological activity of the heart is recoded over time, and it is recoded by capturing signals from an electrode applied to the patient's skin.

The R-waves in an ECG signal may be used to calculate the heartbeat of the user. However, when the T-waves in the ECG signal are too big, these T-waves can be misidentified as R-waves. As a result, an incorrect heartbeat may be calculated. However, if a filter (such as an Infinite Impulse Response (IR) filter) is used directly to filter the T-waves, the ECG signal of a patient with heart disease (e.g., the ECG signal of Premature Ventricular Contraction (PVC) patients) may be filtered directly.

However, the timing of using filter to filter the T-waves in the ECG signal is worthy of discussion.

BRIEF SUMMARY OF THE INVENTION

A heart rate detection device and method are provided to overcome the problems mentioned above.

An embodiment of the invention provides a heart rate detection device. The heart rate detection device may include an electrocardiography (ECG) signal extraction circuit, a detection circuit, a calculation circuit, and a filter. The ECG signal extraction circuit may obtain an ECG signal. The detection circuit may be coupled to the ECG signal extraction circuit, and detect a plurality of R-waves in the ECG signal. The calculation circuit may be coupled to the detection circuit. The calculation circuit uses the first R-wave of the plurality of R-waves as the initial point from which to calculate the standard deviation of the R-waves in each moving window. The calculation circuit determines whether the standard deviation corresponding to each moving window is larger than the first threshold. The calculation circuit determines whether the number of moving windows whose corresponding standard deviation exceeds the first threshold is larger than a second threshold to generate a determination result. In addition, the calculation circuit may determine whether to use the filter to filter the ECG signal based on the determination result.

An embodiment of the invention provides a heart rate detection method. The heart rate detection method is applied to a heart rate detection device. The heart rate detection method may include the following steps. An electrocardiography (ECG) signal extraction circuit in the heart rate detection device obtains an ECG signal. A detection circuit in the heart rate detection device detects a plurality of R-waves in the ECG signal. The calculation circuit in the heart rate detection device takes the first R-wave of the plurality of R-waves as the initial point from which to calculate the standard deviation of the R-waves in each moving window; the calculation circuit determines whether the standard deviation corresponding to each moving window is larger than a first threshold; the calculation circuit determines whether the number of moving windows whose corresponding standard deviation exceeds the first threshold is larger than a second threshold to generate a determination result; and the calculation circuit determines whether to use a filter to filter the ECG signal based on the determination result Other aspects and features of the invention will become apparent to those with ordinary skill in the art upon review of the following descriptions of specific embodiments of a heart rate detection device and method.

BRIEF DESCRIPTION OF THE DRAWINGS

The invention will become more fully understood by referring to the following detailed description with reference to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
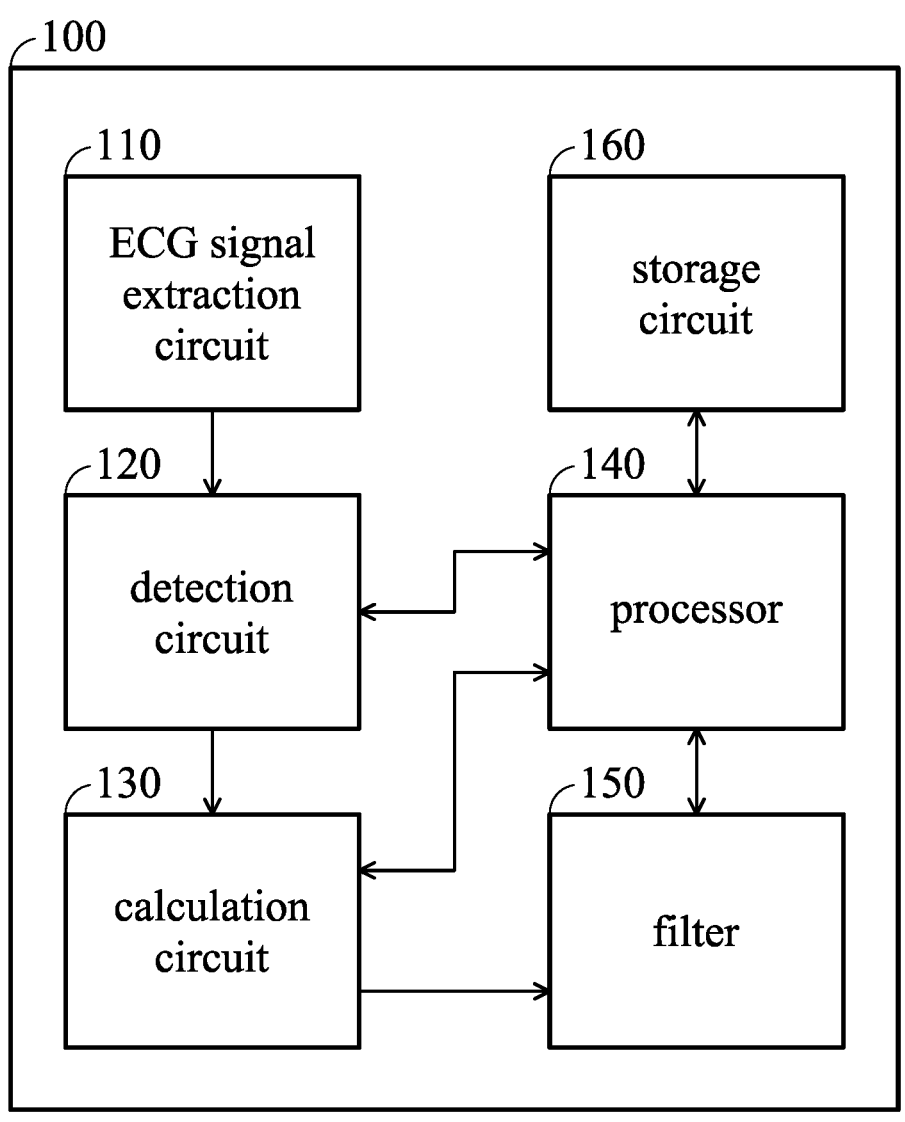
FIG. 1 is a block diagram of a heart rate detection device 100 according to an embodiment of the invention.

FIG. 1 is a block diagram of a heart rate detection device 100 according to an embodiment of the invention. As shown in FIG. 1, the heart rate detection device 100 may comprise a Electrocardiography (ECG) signal extraction circuit 110, a detection circuit 120, a calculation circuit 130, a processor 140, a filter 150, a and a storage circuit 160. It should be noted that FIG. 1 presents a simplified block diagram in which only the elements relevant to the invention are shown. However, the invention should not be limited to what is shown in FIG. 1. The heart rate detection device 100 may also comprise other elements, or one or more of above elements may be combined in one element. For example, the calculation circuit 130 may be combined or integrated in the processor 140.

According to an embodiment of the invention, the ECG signal extraction circuit 110 may measure the ECG signals of the user of heart rate detection device 100, and provide the ECG signals for following operations.

According to an embodiment of the invention, the processor 140 may be configured to control the operations of the ECG signal extraction circuit 110, the detection circuit 120, the calculation circuit 130, the filter 150 and the storage circuit 160. According to another embodiment of the invention, the operations of the detection circuit 120, calculation circuit 130 and filter 150 may be realized by the processor 140 performing relevant programs or codes. The relevant programs or codes may be stored in the storage circuit 160. Details of the operations of detection circuit 120 and calculation circuit 130 are illustrated below.

The filter 150 may be an Infinite Impulse Response (IIR) filter, but the invention should not be limited thereto. The filter 150 may be configured to filter the ECG signal to remove the T-waves which are too big in the ECG signal.

The storage circuit 160 may store the software and firmware program codes, system data, etc. of the heart rate detection device 100. The storage circuit 160 may be a volatile memory (e.g. Random Access Memory (RAM)), or a non-volatile memory (e.g. flash memory, Read Only Memory (ROM)), a hard disk, or a combination of the above memory devices. According to an embodiment of the invention, the storage circuit 160 may store a plurality of applications.

According to an embodiment of the invention, the detection circuit 120 may detect the R-waves in the ECG signal obtained by the ECG signal extraction circuit 110. Because when the T-waves in the ECG signal is too big, the detection circuit 120 may determine that these T-waves as R-waves. Therefore, in the invention, the calculation circuit 130 may further calculate and determine the R-waves detected by the detection circuit 120 to determine whether to use the filter 150 to filter the ECG signal. Then, the detection circuit 120 may detect the R-waves in the filtered ECG signal again.

Figure 2A:
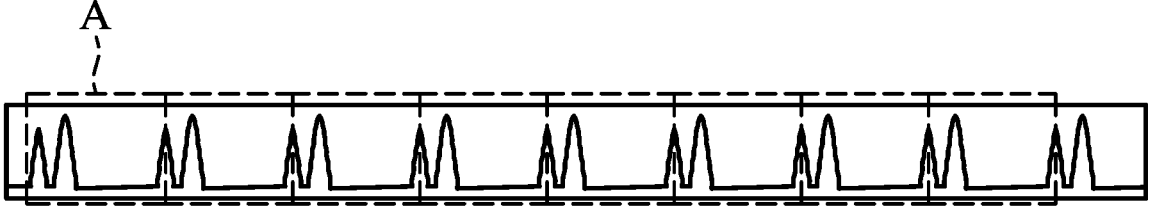
FIGS. 2A-2B are schematic diagrams illustrating moving windows according to an embodiment of the invention.
Figure 2B:
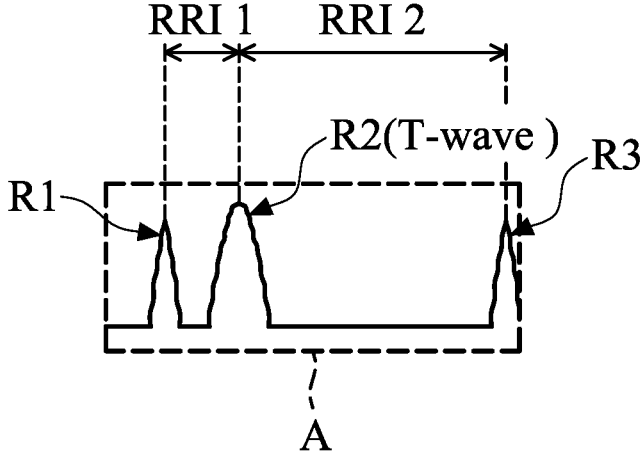

According to an embodiment of the invention, calculation circuit 130 may calculate the standard deviation of R-waves in a moving window according to the R-waves detected by the detection circuit 120. Specifically, the calculation circuit 130 may calculate the R-R intervals (RRIs) between every two R-waves in the moving window, and then calculate the standard deviation of all R-waves in the moving window based on the R-R intervals. Taking FIGS. 2A-2B as an example, each moving window may comprise three R-waves (the second R-wave is T-wave in fact, but in order to illustrate easily, the T-wave may regarded as an R-wave). As shown in FIG. 2B, the calculation circuit 130 may calculate the first R-R interval RRI 1 between the first R-wave R1 and the second R-wave R2 in the moving window A, and calculate the second R-R interval RRI 2 between the second R-wave R2 and the third R-wave R3 in the moving window A. Then, the calculation circuit 130 may calculate the standard deviation corresponding to the moving window A based on the first R-R interval RRI 1 and the second R-R interval RRI 2. Accordingly, the calculation circuit 130 may also calculate the standard deviations corresponding to other moving windows. It should be noted that the above example is only used to illustrate the embodiment of the invention, but the invention should not be limited thereto. In other embodiments, each moving widow may comprise other number of R-waves. In addition, the length of moving window may be different based on the R-waves framed by the moving window. In the embodiment of the invention, the calculation circuit 130 may calculate the standard deviation corresponding to each moving window based on the following equation:

$$\sigma_{win} = \sqrt{\frac{1}{n-1}\sum_{i=n-1}^{n}\left(RRI_i - \overline{RRI}\right)},$$

wherein $\sigma_{win}$ means the standard deviation corresponding to the moving window, n means the number of R-waves in the moving window, $RRI_i$ means the i-th R-R interval, $\overline{RRI}$ means the average of the R-R intervals.

After the calculation circuit 130 calculates the standard deviation corresponding to each moving window, the calculation circuit 130 may determine whether the standard deviation corresponding to each moving window is larger than a first threshold (e.g., 40 (sampling points), but the invention should not be limited thereto). When the standard deviation corresponding to a moving window exceeds the first threshold, the calculation circuit 130 may determine that this moving window is an abnormal moving window (i.e., the moving window may comprise the second R-wave which is a T-wave, when in fact the T-wave is too big, and therefore the T-wave is misidentified as an R-wave). For example, if the standard deviation $\sigma_{win}$ exceeds the first threshold $\sigma_T$, the calculation circuit 130 may determine that this moving window is an abnormal moving window.

Then, the calculation circuit 130 may determine whether the number of abnormal moving windows is larger than a second threshold (e.g., 50%) to determine whether to use the filter 150 to filter the ECG signals.

According to an embodiment of the invention, the second threshold may be a proportional value. According to an embodiment of the invention, if the number of abnormal moving windows is $N_{ab}$ and the total number of moving windows is N, when the proportional value $P_{ab}$ of the number of abnormal moving window $$N_{ab}\left(\text{i.e., } P_{ab} = \frac{N_{ab}}{N}\right)$$

is larger than the second threshold (e.g., 50%), the calculation circuit 130 may determine use the filter 150 to filter the ECG signals to filter the T-waves in the ECG signals. After the filter 150 filters the ECG signals, the detection circuit 120 may detect the R-waves in the ECG signals again, and the calculation circuit 130 may calculate the heart rate of the user based on the re-detected R-waves.

When the proportional value $P_{ab}$ of the number of abnormal moving windows $N_{ab}$ is not larger than the second threshold (e.g., 50%), the calculation circuit 130 may determine not to use the filter 150 to filter the ECG signals, i.e., the calculation circuit 130 may directly calculate the heart rate of the user based on the R-waves detected by the detection circuit 120. That is to say, in this situation, the calculation circuit 130 may determine that the ECG signals may be from the patient with heart disease (e.g., the ECG signal of Premature Ventricular Contraction (PVC) patients). Therefore, the calculation circuit 130 may directly calculate the heart rate of the user based on the R-waves detected by the detection circuit 120. That is to say, the abnormal moving windows (i.e., the T-waves is too big) may occur because that the ECG signals may be from the patient with heart disease. Therefore, the calculation circuit 130 may determine not to use the filter 150 to filter the ECG signals to avoid filtering the features of the heart disease (e.g., the T-waves is too big).

Figure 3A:
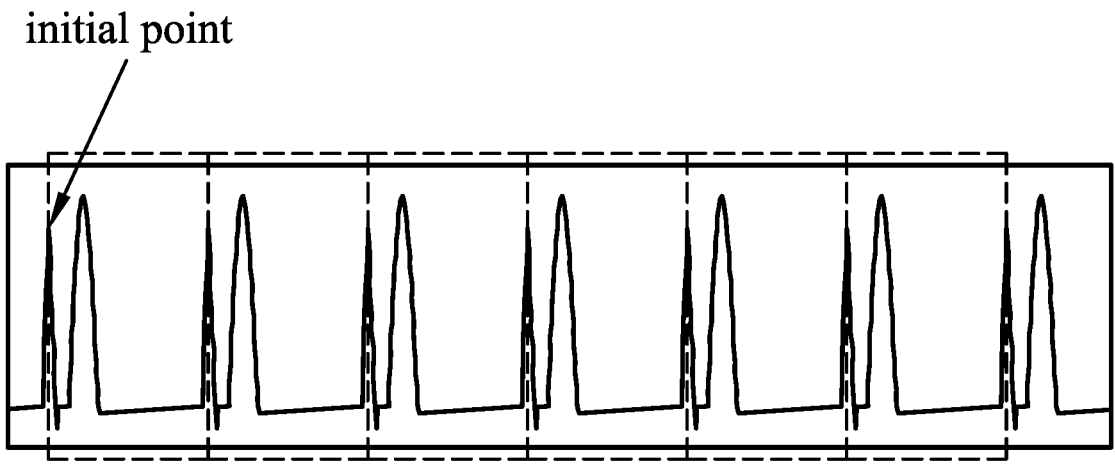
FIGS. 3A-3B are schematic diagrams illustrating a plurality of scan results according to another embodiment of the invention.
Figure 3B:
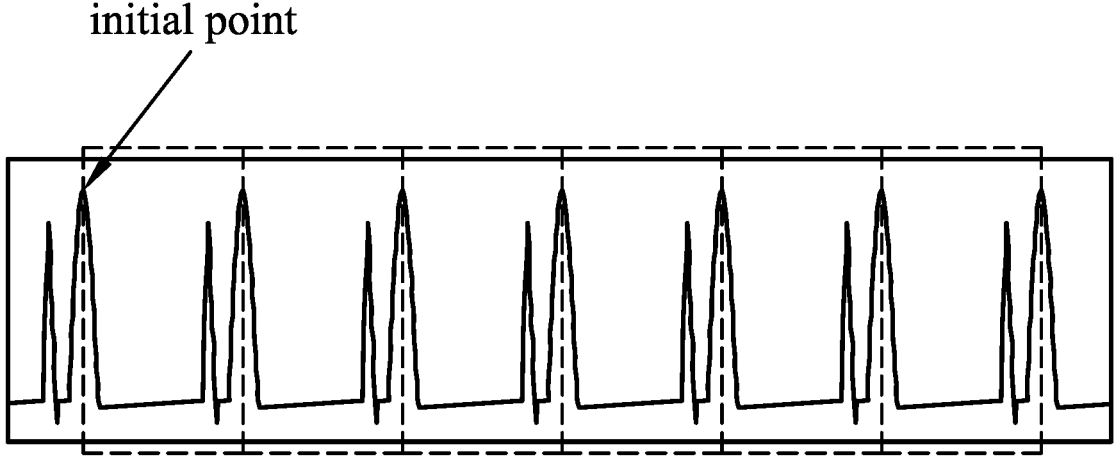

According to another embodiment of the invention, the calculation circuit 130 may determine whether to use the filter 150 to filter the ECG signals based on a plurality of scan results. Taking FIGS. 3A-3B as an example, as shown in FIG. 3A, in the first scan result, the calculation circuit 130 may use the first R-wave of the ECG signal as the initial point, and then determine whether the standard deviation corresponding to each moving window exceeds the first threshold, and determine whether the number of abnormal moving windows is larger than the second threshold. Then, as shown in FIG. 3B, in the second scan result, the calculation circuit 130 may use the second R-wave of the ECG signal as the initial point, and then determine whether the standard deviation corresponding to each moving window exceeds the first threshold, and determine whether the number of abnormal moving windows is larger than the second threshold. When in both of the first scan result and the second result, the calculation circuit 130 determines the proportional value $P_{ab}$ of the number of abnormal moving windows $$N_{ab} \left( \text{i.e., } P_{ab} = \frac{N_{ab}}{N} \right)$$

is larger than the second threshold (e.g., 50%), the calculation circuit 130 may determine use the filter 150 to filter the ECG signals to filter the T-waves in the ECG signals. When only in the first scan result or the second result, the calculation circuit 130 determines the proportional value $P_{ab}$ of the number of abnormal moving windows $$N_{ab} \left( \text{i.e., } P_{ab} = \frac{N_{ab}}{N} \right)$$

is larger than the second threshold (e.g., 50%), the calculation circuit 130 may determine not use the filter 150 to filter the ECG signals to filter the T-waves in the ECG signals, i.e., the calculation circuit 130 may directly calculate the heart rate of the user based on the R-waves detected by the detection circuit 120. When in both of the first scan result and the second result, the calculation circuit 130 determines the proportional value $P_{ab}$ of the number of abnormal moving windows $$N_{ab} \left( \text{i.e., } P_{ab} = \frac{N_{ab}}{N} \right)$$

is not larger than the second threshold (e.g., 50%), the calculation circuit 130 may determine not use the filter 150 to filter the ECG signals to filter the T-waves in the ECG signals, i.e., the calculation circuit 130 may directly calculate the heart rate of the user based on the R-waves detected by the detection circuit 120. It should be noted that the example of FIGS. 3A-3B is only used to illustrate the embodiment of the invention, but the invention should not be limited thereto. The calculation circuit 130 may adopt more number of scan results.

Figure 4:
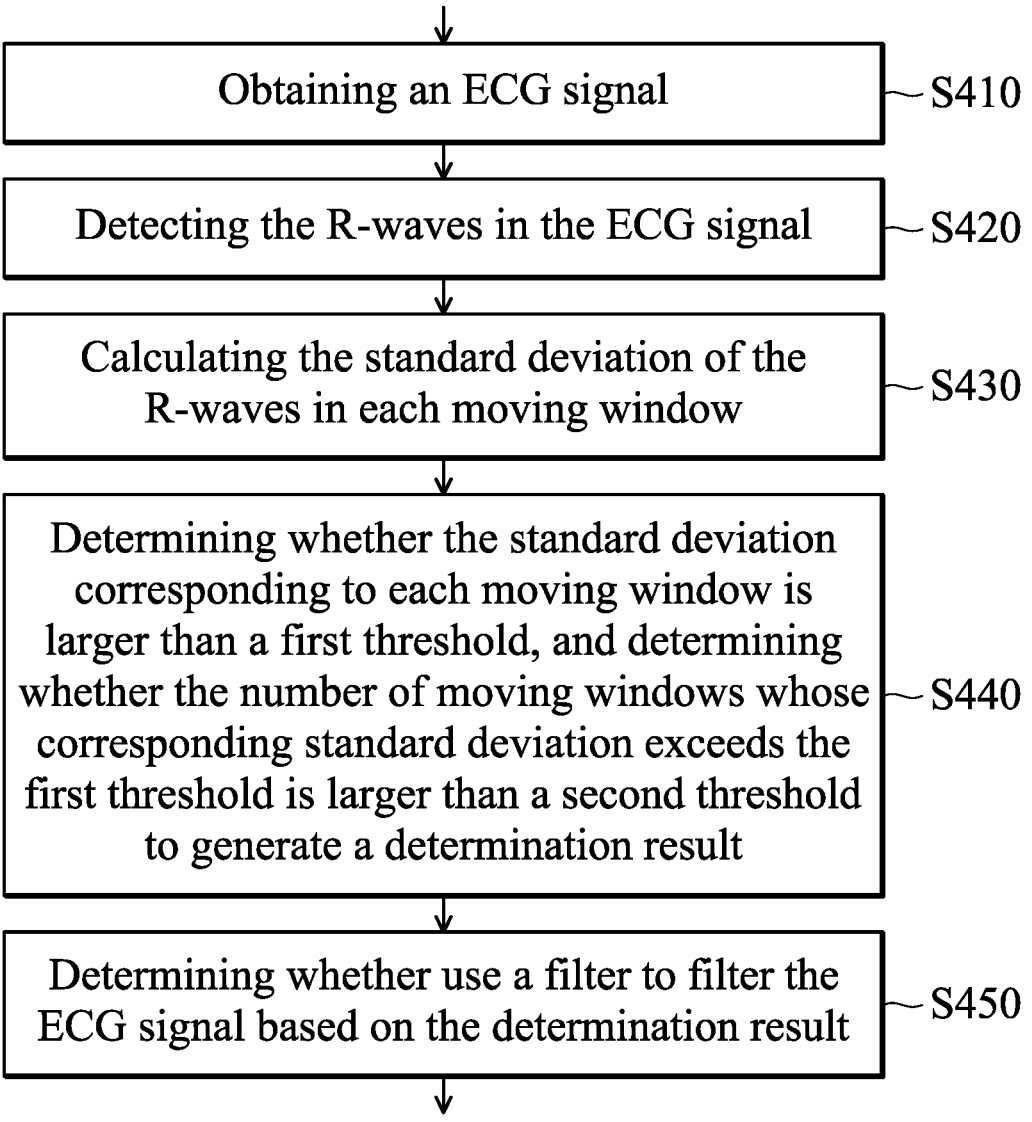
FIG. 4 is a flow chart illustrating a heart rate detection method according to an embodiment of the invention.

FIG. 4 is a flow chart illustrating a heart rate detection method according to an embodiment of the invention. The heart rate detection method can be applied to the heart rate detection device 100. As shown in FIG. 4, in step S410, the ECG signal extraction circuit in the heart rate detection device 100 may obtain an ECG signal.

In step S420, the detection circuit in the heart rate detection device 100 may detect the R-waves in the ECG signal.

In step S430, the calculation circuit in the heart rate detection device 100 may use the first R-wave of the R-waves as the initial point from which to calculate the standard deviation of the R-waves in each moving window.

In step S440, the calculation circuit in the heart rate detection device 100 may determine whether the standard deviation corresponding to each moving window is larger than a first threshold, and determine whether the number of moving windows whose corresponding standard deviation exceeds the first threshold is larger than a second threshold to generate a determination result.

In step S450, based on the determination result, the calculation circuit in the heart rate detection device 100 may determine whether use a filter to filter the ECG signal. According to an embodiment of the invention, the filter may be an Infinite Impulse Response (IR) filter.

According to an embodiment of the invention, step S450 may further comprise that when the determination result is that the number of moving windows whose corresponding standard deviation exceeds the first threshold is not larger than the second threshold, the calculation circuit in the heart rate detection device 100 may directly adopt the ECG signal to calculate the heart rate (i.e., the filter is not used). When the determination result is that the number of moving windows whose corresponding standard deviation exceeds the first threshold is larger than the second threshold, the calculation circuit in the heart rate detection device 100 may determine to use the filter to filter the ECG signal, and after the filter has filtered the ECG signal, the detection circuit in the heart rate detection device 100 may detect the R-waves in the ECG signal again.

According to an embodiment of the invention, the heart rate detection method may further comprise the following steps. The calculation circuit in the heart rate detection device 100 may use the second R-wave of the R-waves as the initial point from which to calculate the standard deviation of the R-waves in each moving window. The calculation circuit determines whether the standard deviation corresponding to each moving window exceeds the first threshold. The calculation circuit determines whether the number of moving windows whose corresponding standard deviation exceeds the first threshold is larger than the second threshold. When the first R-wave is used as the initial point and the number of moving windows whose corresponding standard deviation exceeds the first threshold is larger than the second threshold, and the second R-wave is used as the initial point and the number of moving windows whose corresponding standard deviation exceeds the first threshold is larger than the second threshold, then the calculation circuit in the heart rate detection device 100 may determine to use the filter to filter the ECG signal.

According to the heart rate detection method provided in the invention, the heart rate detection device may determine whether to use the filter to filter the T-waves in the ECG signal. Therefore, according to the heart rate detection method provided in the invention, it will be able to avoid that when the filter is directly used to filter the T-waves, the ECG signal of the patients with heart disease (e.g., the ECG signal of Premature Ventricular Contraction (PVC) patients) may be filtered directly.

Use of ordinal terms such as "first", "second", "third", etc., in the disclosure and claims is for description. It does not by itself connote any order or relationship.

The steps of the method described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/ processor (which may be referred to herein, for convenience, as a "processor") such that the processor can read information (e.g., code) from and write information to the storage medium. A sample storage medium may be integral to the processor. The processor and the storage medium may reside in an ASIC. The ASIC may reside in user equipment. Alternatively, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

The above paragraphs describe many aspects. Obviously, the teaching of the invention can be accomplished by many methods, and any specific configurations or functions in the disclosed embodiments only present a representative condition. Those who are skilled in this technology will understand that all of the disclosed aspects in the invention can be applied independently or be incorporated.

While the invention has been described by way of example and in terms of preferred embodiment, it should be understood that the invention is not limited thereto. Those who are skilled in this technology can still make various alterations and modifications without departing from the scope and spirit of this invention. Therefore, the scope of the present invention shall be defined and protected by the following claims and their equivalents.

What is claimed is:

1. A heart rate detection device, comprising:
an electrocardiography (ECG) signal extraction circuit, obtaining an ECG signal;
a detection circuit, coupled to the ECG signal extraction circuit, and detecting a plurality of R-waves in the ECG signal;
a calculation circuit, coupled to the detection circuit, taking a first R-wave of the plurality of R-waves as an initial point to calculate a standard deviation of the R-waves in each moving window, determining whether the standard deviation corresponding to each moving window is larger than a first threshold, and determining whether a number of the moving windows whose corresponding standard deviation is larger than the first threshold is larger than a second threshold to generate a determination result; and
a filter, coupled to the calculation circuit;
wherein the calculation circuit determines whether to use the filter to filter the ECG signal based on the determination result,
wherein when the determination result is that the number of the moving windows whose corresponding standard deviation is larger than the first threshold is not larger than the second threshold, the calculation circuit determines not to use the filter.

2. The heart rate detection device of claim 1, wherein the filter is an Infinite Impulse Response (IIR) filter.

3. The heart rate detection device of claim 1, wherein when the determination result is that the number of the moving windows whose corresponding standard deviation is larger than the first threshold is larger than the second threshold, the calculation circuit determines to use the filter to filter the ECG signal, and after the filter has filtered the ECG signal, the detection circuit detects the R-waves in the ECG signal again.

4. The heart rate detection device of claim 1, wherein the calculation circuit takes a second R-wave of the R-waves as the initial point to calculate the standard deviation of the R-waves in each moving window, and determine whether the standard deviation corresponding to each moving window is larger than the first threshold, and determine whether the number of the moving windows whose corresponding standard deviation is larger than the first threshold is larger than the second threshold, and wherein when the first R-wave is used as the initial point and the number of the moving windows whose corresponding standard deviation is larger than the first threshold is larger than the second threshold, and when the second R-wave is used as the initial point and the number of the moving windows whose corresponding standard deviation is larger than the first threshold is larger than the second threshold, the calculation circuit determines to use the filter to filter the ECG signal.

5. A heart rate detection method, applied to a heart rate detection device, comprising:
obtaining, via an electrocardiography (ECG) signal extraction circuit in the heart rate detection device, an ECG signal;
detecting, via a detection circuit in the heart rate detection device, a plurality of R-waves in the ECG signal;
using, via a calculation circuit in the heart rate detection device, a first R-wave of the plurality of R-waves as an initial point to calculate a standard deviation of the R-waves in each moving window;
determining, via the calculation circuit, whether the standard deviation corresponding to each moving window is larger than a first threshold;
determining, via the calculation circuit, whether a number of the moving windows whose corresponding standard deviation is larger than the first threshold is larger than a second threshold to generate a determination result;
determining, via the calculation circuit, whether to use a filter to filter the ECG signal based on the determination result; and
determining, via the calculation circuit, not to use the filter when the determination result is that the number of the moving windows whose corresponding standard deviation is larger than the first threshold is not larger than the second threshold.

6. The heart rate detection method of claim 5, wherein the filter is an Infinite Impulse Response (IIR) filter.

7. The heart rate detection method of claim 5, further comprising:
determining, via the calculation circuit, to use the filter to filter the ECG signal when the determination result is that the number of the moving windows whose corresponding standard deviation is larger than the first threshold is larger than the second threshold; and
detecting, via the detection circuit, the R-waves in the ECG signal again after the filter has filtered the ECG signal.

8. The heart rate detection method of claim 5, further comprising:
taking, via the calculation circuit, a second R-wave of the R-waves as the initial point to calculate the standard deviation of the R-waves in each moving window;
determining, via the calculation circuit, whether the standard deviation corresponding to each moving window is larger than the first threshold, and determining whether the number of the moving windows whose corresponding standard deviation is larger than the first threshold is larger than the second threshold; and determining, via the calculation circuit, to use the filter to filter the ECG signal when the first R-wave is used as the initial point and the number of the moving windows whose corresponding standard deviation is larger than the first threshold is larger than the second threshold, and when the second R-wave is used as the initial point and the number of the moving windows whose corresponding standard deviation is larger than the first threshold is larger than the second threshold.

\* \* \* \* \*